United States Patent [19]

Williams et al.

[11] Patent Number: 5,576,013
[45] Date of Patent: Nov. 19, 1996

[54] TREATING VASCULAR AND NEOPLASTIC TISSUES

[75] Inventors: Patricia B. Williams, Norfolk; John D. Sheppard, Cape Charles, both of Va.

[73] Assignee: Eastern Virginia Medical School, Norfolk, Va.

[21] Appl. No.: 408,000

[22] Filed: Mar. 21, 1995

[51] Int. Cl.$^6$ ................................ A61F 2/02; A61K 9/70; A61L 15/16

[52] U.S. Cl. .................... 424/423; 424/427; 424/443; 424/445; 424/449

[58] Field of Search ........................... 424/423, 427, 424/443, 445, 449; 604/21

[56] References Cited

U.S. PATENT DOCUMENTS

| | | | |
|---|---|---|---|
| 4,932,934 | 6/1990 | Dougherty et al. | 604/21 |
| 5,279,298 | 1/1994 | Flower | 128/633 |

OTHER PUBLICATIONS

Roberts et al., "Role of neovasulature and vascular permeability on tumor retention of photodynamic agents", Cancer Res (1992), 52(4), 924–30 (Abstract only).

Mendelsohn et al., "Ameleriotion . . . by photochemical induced thrombosis of feeder vessels," Arch of Ophthalmol. (Chicago) 1987, 105(7), 983–8 (Abstract only).

*Primary Examiner*—Carlos Azpuru
*Attorney, Agent, or Firm*—Banner & Allegretti, Ltd.

[57] ABSTRACT

Lesions supplied by abnormal aggregations of vascular tissue or neovascular tissues are treated with photodynamic therapy by application of photosensitizing agent followed by precisely directed and calibrated laser activation to induce photothrombosis within target vascular tissue. The treatment forms a blood clot within the supply vessels thereby reducing the blood supply to the target lesion. Treated tissues atrophy or recede with low regrowth of vessels. The lower energy levels required significantly reduce damage to the surrounding tissues.

16 Claims, No Drawings

TREATING VASCULAR AND NEOPLASTIC TISSUES

FIELD OF THE INVENTION

The invention relates to a method for treating vascular, neovascular, and neoplastic tissues (collectively "lesions") with photodynamic therapy utilizing a laser and topically applied photosensitizing agents.

BACKGROUND OF THE INVENTION

Photodynamic therapy (PDT) involves the use of light energy in the treatment of one or more afflictions. The field is broad enough to encompass light in a variety of forms from visible light to organized light energy such as that emitted by lasers. Such treatments can be used as an alternative to traditional chemotherapy and surgical treatments and thereby avoid the side effects and drawbacks associated therewith.

Early work in the 1970's, followed by rapidly expanding studies in the 1980's, has shown that photodynamic therapy (PDT) offers a viable, less toxic and generally less painful avenue to treatment of certain lesions. In PDT, photosensitizing dyes are administered to a patient and localize in neoplastic tissues. The great majority of the earlier PDT agents studied have been derived from natural sources (porphyrins, chlorins, purpurins, etc.) or from known chemicals originating in the dyestuffs industry (e.g., cyanine dyes). For more recent PDT agents derived from natural sources see U.S. Pat. Nos. 4,961,920 and 4,861,876. Synthetic efforts have focused on porphryinoid compounds which are highly absorptive in the longer wavelength range of about 600–1200 nm, where the transparency of tissue is higher. Compounds such as purpurines, naphthocyanin silicon complexes, chlorins, bacteriochlorins, and substituted phenylporphyrins have been prepared and tested in vivo. Additional PDT agents are described in EP 276,121 and Weinstein et al. U.S. Pat. No. 4,753,958 (the disclosure of which is herein incorporated by reference).

Irradiation of the porphyrinoid dye with light at a wavelength which corresponds to an absorption band of the dye results in destruction of the neoplastic vascular tissue. The use of a fiber optic laser light source is described in U.S. Pat. No. 4,957,481. PDT has been used to treat a variety of tumors including bladder, bronchial, bone marrow and skin tumors as well as severe psoriasis.

Dougherty et al (Cancer Res., 1978, 38:2628; Photochem. Photobiol, 1987, 45:879) pioneered the field with infusion of photoactivatable dyes, followed by appropriate long wavelength radiation of the tumors (600+nm) to generate a lethal shortlived species of oxygen which destroyed the neoplastic cells. Early experiments utilized a mixture termed hematoporphyrin derivative (HPD). The deficiencies of HPD, especially prolonged phototoxicity caused by retained HPD components in human skin led to its displacement by a purified fraction termed dihematoporphyrin ether (DHP) which, although yielding improvements over HPD, nevertheless still suffered certain, practical limitations. Relatively weak absorption in the wavelength range above 600 nm, retention in dermal cells (potentially leading to phototoxicity), only modest or low selectivity for tumor cells versus other cell types in vital organs, the inability to use available, modern, inexpensive diode lasers, and uncertain chemical constitution of the mixtures are all known negative features of DHP and HPD. In animal and cell culture experiments one observes, following PDT, depending on the incubation time, damage to the vasculature, cell membranes, mitochondria and specific enzymes. See, U.S. Pat. No. 5,179,120.

Prior efforts with PDT have been directed at neoplastic tissue destruction with the energy of the laser. Such therapy has, however, had limited success due to the damage caused to surrounding tissues from the high laser energies required to destroy the target tissue. It would be useful to have a method for treating neoplastic vascular tissues that did not require such high applied energy levels or which was accompanied by damage to adjacent non-target tissues.

Weinstein et al. U.S. Pat. No. 4,753,958 teaches the PDT treatment of hyperproliferative epithelial diseases with phototoxic levels of hematoporphyrin in a topical formulation. The sensitizer was determined to inhibit DNA synthesis in treated tissues following photoactivation. To block cell division in the diseased tissue, sensitized tissue is irradiated in its entirety with a radiation source selected from UVA, fluorescent light, high intensity incandescent light, 1600 and 5000 Watt xenon arc lamps, red dye lasers, or a slide projector filtered to pass light of wavelengths no longer than 600 nm. The examples show that the illumination source is broadly directed to the entirety of the light sensitized tissue area to activate a cytotoxic response in the diseased tissue. The applied DHP is activated under the effects of light produces free radicals or singlet oxygen molecules. These produce cytotoxic oxygen products which, in turn, produce a cyto-destructive effect in abnormal human tissues.

Unfortunately, the broad area treatment taught by Weinstein et al. requires a power and a dispersion area sufficient to activate a cytotoxic response throughout the treated tissue. The laser energy required for such an affect is about 30–370 $J/cm^2$, typically about 320 $J/cm^2$ although the precise radiation dose is not considered to be critical. See, Weinstein et al. in column 8, lines 47–48. Such a dispersion pattern affects nontarget tissues immediately surrounding the target tissue.

It would be desirable to have a photodynamic treatment that was highly specific to the desired target tissues.

Additionally, Weinstein et al. is limited to the treatment of external epithelial tissues. Certain lesions occur in tissues (e.g., mucous membrane tissues like ocular tissue and gastrointestinal tract tissues) that do not contain cutaneous epithelial cells would benefit from photodynamic therapy as would tissues exposed surgically, e.g., nerves, muscles, and tumors. It would be desirable to have an effective photodynamic treatment therapy for tissues other than epithelial tissues.

Corneal neovascularization (CNV) is a major problem in corneal disease. Corneal vessels are always anatomically abnormal and represent a disease process. Abnormal blood vessels may form in the cornea from physical insult and injury, infections, chemical burns, corneal allograph rejection, prolonged hypoxia from chronic abusive contact lens use, or from chronic immunological activation as seen in herpetic stromal keratitis. These new corneal vessels can be at any depth within the cornea. In severe cases, the vessels can impinge upon the visual axis or produce abnormal exudates, thus affecting vision.

Patients with CNV are predisposed to a marked increase in the risk of corneal allograft rejection. The abnormal vessels provide circulating lymphocytes with ready access to donor cornea that would otherwise be granted immune privilege away from the normal conjunctival vascular arcades. Patients with CNV may have allograft survival rams as low as 35% compared with the more typical 90% rate. Thus, CNV represents one of the most important risk factors for corneal allograph rejection.

Laser treatments have been attempted for ablating individual corneal vessels. In practice, however, this therapy failed to produce favorable long term results because the energy required to coagulate CNV is so intense that subsequent inflammation may actually induce the formation of additional CNV.

It would be desirable to have a treatment for CNV that would be effective and without injury to the adjacent healthy corneal tissue.

Unfortunately, established CNV is very difficult to eradicate. New vessels may remain to the detriment of the patient even when the initial stimulus for CNV formation is removed.

SUMMARY OF THE INVENTION

In accordance with the invention herein, a treatment according to the invention comprises:

applying a photosensitizing agent to target tissue consisting essentially of tissues containing blood-carrying vessels supplying an undesired lesion, the photosensitizing agent being in a pharmaceutically acceptable composition for contact with said target tissue;

illuminating an area consisting essentially of the treated blood-carrying vessels with light from a laser emitting light of a frequency and energy which excites the photosensitizing agent and coagulates blood in said vessels.

With the photodynamic treatment of the invention, lesions and abnormal collections of vascular tissue can be treated with a high degree of precision with little or no damage to adjacent tissues. Rather than seek to induce DNA-level changes in the target tissue, the present invention is directed to treating the blood-supplying vascular tissue to induce photothrombosis. Once the blood supply is blocked, the target lesion involutes and dies. Such a specific process requires less energy than with previous tissue destruction-based methods and exhibits less non-target tissue damage.

DETAILED DESCRIPTION

Vascular tissue of neoplastic and neovascular lesions as well as abnormal collections of vascular tissue are sensitized to light by the topical application of a light sensitizing agent. When later exposed to laser energy of a level sufficient to induce intravascular coagulation, i.e., a blood clot inside the vessel blocking blood flow through the vessel, rather than burn or destroy the tissues. Because the rapidly proliferating target tissues have a higher need for blood supply than adjacent healthy tissues, the target tissues are relatively more sensitive to the loss of a blood supply and are selectively affected. As the vascular tissue atrophies, the blood supply for the lesion or target vascular tissue continues to decrease to the detriment of the target lesion. As a result, lesions clear, and vascular tissue regresses or atrophies.

Method of Use

The topical sensitizing agent is applied to the tissues containing the target vessels several times a day for 1–14 days. Following the last application, no sensitizing agent is applied for a period of 1–7 days to allow removal of sensitizing agent from adjacent tissues while high concentrations are maintained in the tissues containing the target vessels.

The present invention provides particular benefits from a higher degree of selectivity in the treated tissues. The spot size of the laser and duration of the exposure should be adjusted depending on the dimensions and location of the lesion vascular tissue or target vessel to contact not substantially more than the surface of discernible target vessels. Preferably, the spot size of the laser is within the range of about 25 microns to about 2000 microns with exposure times on the order of pico seconds up to one second. The specific size and duration will necessarily depend on the strength of the laser being used, the diameter of the target vessel, the presence or absence of pigmentation, and the ability to discern specific target vessels.

Highly pigmented lesions may hinder the location of specific target vessels and require light treatment over a somewhat broader area where target vessels are thought to reside but not significantly outside that area. Such treatments continue to be at an energy level just sufficient to induce photothrombosis. This energy level is still lower than that used for general tissue irradiation leading to tissue destruction or genetic changes.

The laser energy delivered to the target vessels per light burst in the present invention is within the range from about 1 Joule/cm$^2$ (J/cm$^2$) to about 4000 J/cm$^2$, preferably within the range from about 1–300 J/cm$^2$, and more preferably within the range from about 10 J/cm$^2$ to about 200 J/cm$^2$. Typical treatments may involve anywhere from 10 to 4000 applications of laser energy to one or more target vessels supplying blood to a lesion. The energy levels effective for blood coagulation in comparable lesions represent a reduction in applied energy of roughly 10 times less energy than a general tissue irradiation treatment as in Weinstein et al. U.S. Pat. No. 4,753,958. (The energy required to affect the DNA propagation character of treated epithelial cells is about 320 J/cm$^2$.) The lower power used in the present treatment decreases post-operative inflammation and the stimulus for additional vessel growth.

The applied energy level can also be adjusted by the number of times the energy is applied. The specific number of such "shots" will depend on the target lesion. Some lesions may require 200 shots to effect photothrombosis, others only 10–50 shots, while others may need 3–4 sessions of 100 shots each.

Successful and sufficient treatment is not determined immediately after cessation of the treatment. Usually, within 24 hours damage to target vessels, hemorrhaging, and damage to distal blood flow can be seen. Continuing shrinkage of the target vessels continues thereafter for successfully treated vessels. More definitive determinations can be made after about 90 days when the need for retreatment can be determined.

Target Tissues

Tissues that can be treated by the present invention include the vascular tissue in corneal tissue and other ocular and extraocular tissues accessible for topical application of photosensitizing agents; mucous membrane tissues including upper and lower respiratory tract tissues, gastrointestinal tract tissues, genitourinary tract tissues (male and female), cutaneous tissue, buccal (oral) tissues; and surgically exposed tissues such as intracranial tissue, intraperitoneal tissue, intra articular tissue, bone, connective tissue, and cardiovascular tissue, and neural tissues in the brain or spinal cord.

Lesions and abnormal collections of unwanted vascular tissue that can be treated by the present invention include tumors, inflammatory or post-traumatic scars, abscesses, neovascularization (abnormal blood vessels), telangiectasias (redundant vessel aggregates) as in rosacea, condylomata (warts), nevi (moles), hemangiomas (port wine stains), cafe-au-lait spots (coffee spots), other abnormal pigmented lesions, and tattoos.

Photosensitizing Agents

Photosensitizing agents that can be used are those that will render blood in target tissues sensitive to coagulation from exposure to light. Exemplary agents and a few of the light frequencies to which they are sensitive include pyrromethane boron difluorides, indocyanine green, zinc phthalocyanine, dihematoporphyrin (514 nm), benzoporphyrin derivatives, carotenoporphyrins, hematoporphyrin and porphyrin derivatives, rose bengal (550 nm), bacteriochlorin A (760 nm), epigallocatechin, epicatechin derivatives, hypocrellin B, urocanic acid, indoleacrylic acid, rhodium complexes, etiobenzochlorins, octaethylbenzochlorins, sulfonated Pc-naphthalocyanine, silicon naphthalocyanines, chloroaluminum sulfonated phthalocyanine (610 nm), phthalocyanine derivatives, iminium salt benzochlorins and other iminium salt complexes, Merocyanin 540, Hoechst 33258, and other DNA-binding fluorochromes, psoralens, acridine compounds, suprofen, tiaprofenic acid, non-steroidal anti-inflammatory drugs, methylpheophorbide-a-(hexyl-ether) and other pheophorbides, furocoumarin hydroperoxides, Victoria blue BO, methylene blue, toluidine blue, porphycene compounds as described in U.S. Pat. No. 5,179,120 (the entire contents of which are herein incorporated by reference), and any other photosensitizing agents. The preferred sensitizing agents are benzoporphyrin derivatives, dihematoporphyrin (514 nm), hematoporphyrin, porphyrin derivatives, indocyanines, and phthalocyanines.

Sensitizing agents used in the present invention are brought into contact with the vascular tissue in target lesions by topical application or direct injection into the target tissue. Such applications are intended to selectively sensitize the target lesion and avoid the adverse general light sensitivity found with conventional intravenous administration of sensitizing agents.

Topical Formulations

Unformulated photosensitizing agents cannot be applied topically and be effective for photodynamic therapy. The agents would not adhere properly, would immediately diffuse away from the target tissues, would remain unstable in storage and through transportation, would be susceptible to bacterial contamination, and would not be readily applied. Storage and delivery formulations are used to overcome such problems. Suitable formulations will be in combination with penetrating solvents or be in the form of a gel, lotion, cream, or ointment containing a sufficient amount of light sensitizing agent to be effective with photodynamic therapy. See, U.S. Pat. No. 5,179,120.

The photosensitizing agents may be formulated for topical application in penetrating solvents or in the form of a lotion, cream, ointment or gel containing a sufficient amount of the photosensitizing agent compound to be effective for PDT therapy. Such topical formulations may be prepared in gel form by combining the photosensitizing agent with a solvent and adding a gelling agent thereto. Suitable gelling agents include carboxymethyl cellulose (Carbopol™ 934P from B. F. Goodrich of Brecksville, Ohio U.S.A.) and fumed silica (CAB-O-SIL®, Cabot Corp., Tuscola, Ill.). The gelling agent is generally used in amounts of about 5–10 wt % to obtain a gel with the desired viscosity. Obviously, gels containing more or less gelling agent will have slightly higher or lower viscosity. One skilled in the art can readily obtain the desired gel viscosity by adjusting the concentration of gelling agent.

Additives, such as cosolvents, surfactants and/or bioadhesives frequently improve the gel properties and may be added as desired. Suitable cosolvents/surfactants include propylene glycol and glycerine. Suitable bioadhesives include carboxymethylcellulose, polyacrylic polymers, chitosan and sodium alginate, modified starch with polyacrylic polymers, eudispert hv hydrogels or xerogels, sodium hyaluronate, and polymers of polyethylene glycol, hydroxypropylcellulose, or carboxyvinyl. The additives may be incorporated into the gel by mechanically mixing the additives into a mixture of solvent and gelling agent.

Other additives may be used to enhance or maintain chemical stability and physiological suitability. Examples are antioxidants, chelating agents, inert gases, buffers and isotonicifiers. Examples of antioxidants and typical concentration ranges include acetone sodium bisulfite (0.1–0.8%), ascorbic acid (0.05–1.0%), monothioglycerol (0.1–1.0%), potassium metabisulfite (0.05–0.1%), propyl gallate (0.02%), sodium bisulfite (0.01–1.0%), sodium formaldehyde sulfoxylate (0.03–0.1%), sodium metabisulfite (0.02–0.25%), sodium sulfite (0.01–0.1%), sodium thioglycolate (0.05–0.1%).

Examples of chelating/complexing agents and typical concentration ranges include edetate sodium (0.005–0.1%), edetate calcium disodium (0.005%–0.01%), gentisic acid ethanolamide (1.0%–2.0%), niacinamide (1.0%–2.5%), sodium citrate (0.01%–2.5%), citric acid (0.001%–1.0%).

Buffers are used primarily to stabilize a formulation against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH dependent partition into the target malignant tissues or lesion area. Examples of such buffer systems include the following acids: acetic, adipic, ascorbic, benzoic, citric, glycine, lactic, tartaric, hydrochloric, phosphoric, sulfuric, carbonic and bicarbonic; and their corresponding salts such as: potassium, sodium, magnesium, calcium and diethanolamine salts.

When the solution will be dispensed from multiple dose containers, antimicrobial agents in bacteriostatic or fungistatic concentrations are added in amounts effective to provide protection from bacteria or fungi. Among the compounds and concentrations most frequently employed are phenylmercuric acid (0.002–0.01%), thimerosal (0.01%), benzethonium chloride (0.01%), benzalkonium chloride (0.01%), phenol or cresol (0.5%), chlorbutanol (0.5%), benzyl alcohol (2.0%), methyl p-hydroxybenzoate (0.18%), propyl, p-hydroxybenzoate (0.02%), and ethylenediaminetetraacetic acid (EDTA).

Suitable penetrating solvents are solvents for the porphycene compound which will enhance percutaneous penetration of the porphycene compound. Solvents which have this property include proparacaine, dimethyl sulfoxide, dimethyl acetamide, dimethylformamide, 1-methyl-2-pyrrolidone, diisopropyladipate, diethyltoluamide and to a lesser extent propylene glycol. Additional solvents include substituted azacycloalkan-2-ones having from 5 to 7 carbons in the cycloalkyl group such as 1-dodecylazacycloheptan-2-one (AZONE) and other azacycloalkan-2-ones such as described in U.S. Pat. No. 3,989,816 incorporated herein by reference. Also included are N-bis-azocyclopentan-2-onyl alkanes described in U.S. Pat. No. 3,989,815 (hereby incorporated by reference), 1-substituted azacyclopentan-2-ones described in U.S. Pat. No. 3,991,203 (hereby incorporated by reference) and water-soluble tertiary amine oxides described in U.S. Pat. No. 4,411,893 (hereby incorporated by reference).

The topical formulations contain a sufficient amount of the photosensitizing compound to be effective in PDT therapy. Generally, concentrations in the range of 0.001 to 25 wt. %, preferably from about 1 to 5 wt. %, may be used.

The photosensitizing agents can be used with solvents and adjuvants appropriate to the photosensitizing agent chemistry to adjust the viscosity of the formulation. The most important solvents in this group are ethanol, polyethylene glycols of the liquid series and propylene glycol. A more comprehensive listing includes acetone, dimethyl acetamide, dimethyl formamide, dimethyl sulfoxide ethanol, glycerin, polyethylene glycol 300, and 400, propylene glycol, sorbitol, polyoxyethylene sorbitan fatty acid esters such as laureate, palmitate, stearate, and oleate, polyoxyethylated vegetable oil, sorbitan monopalmitate, 2-pyrrolidone; n-methyl-2-pyrrolidine; n-ethyl- 1 -pyrrolidine; tetrahydrofurfuryl alcohol, tween 80 and dimethyl isosorbide. Dimethyl isosorbide (ARLASOLVE® DMI, ICI Specialty Chemicals) has the advantage of being both water- and oil-soluble. Additionally, dimethyl isosorbide may be readily gelled with a gelling agent to produce gel formulations with, for example, 4% KLUCEL® (Hercules).

Additional topical formulations which may be used for the chosen photosensitizing agent are disclosed in U.S. Pat. Nos. 3,592,930 and 4,017,615 which are hereby incorporated by reference.

In a preferred formulation, the photosensitizing agent is applied in an aqueous gel formulation suitable for use on ocular tissues and other such sensitive tissues. Such formulations may contain photosensitizing agent in an amount within the range from about 0.1–20 mg/ml in the formulation, ophthalmologically acceptable penetration enhancers (e.g., proparacaine), and one or more bioadhesive polymers. Preferably, the gel formulation will have a viscosity within the range from about 26,000 to about 1,500,000 cps at 20° C. and a pH compatible with body tissues.

Light Sources

Light in a plurality of bursts from a laser is then applied to one or more target vessels (if discernible) or to lesion tissues thought to contain such vessels. On outer cutaneous, ocular, and buccal surfaces, the energy can be applied directly. Internal mucous membrane surfaces may require appropriate speculum retraction or endoscopic delivery. Preferably, fiber optic lasers are used to deliver the energy with a high degree of precision.

Conventional monochromatic light sources can be used in the present invention by matching the wavelength of the emitted light to the sensitizing wavelength of the photosensitizing agents. Examples include monochromatic light from traditional Argon lasers, tunable dye lasers, pulsed metal vapor lasers (e.g., gold vapor, copper vapor pumped dye lasers, Nd:YAG pumped dye lasers), and solid state lasers. The traditional argon laser is recognized as a standard, readily available laser used in virtually all clinics and hospitals. For these reasons, it is the preferred laser device for use in the present treatment with photosensitizers employed that are sensitive to the green light produced thereby.

EXAMPLES

Example 1

A formulation effective for photodynamic therapy according to the invention is prepared with the materials listed in table 1.

TABLE 1

| Ingredient | Concentration |
|---|---|
| DHP (photosensitizing agent) | 75 mg |
| EDTA (preservative) | 30 mg |
| carboxymethylcellulose (viscosity agent) | 600 mg |
| isotonic saline (diluent) | 30 ml |

The photosensitizing gel formulation is made by adding the carboxymethylcellulose polymer to 10.5 ml saline and titrating to a pH of about 4.5 with 2.0N HCl. This mixture is stirred until a gel is formed whereupon the gel is heat sterilized. The porphyrin and EDTA are dissolved in sterile saline to a final volume of 10 ml and filter sterilized. Under aseptic conditions, the porphyrin/EDTA solution is added to the gel. The pH is adjusted to about 7.4 with 2.0N sterile NaOH. Additional sterile saline is added to make a final volume of about 30 ml. The gel can be refrigerated at about 4° C. until required.

Example 2

The gel of example 1 was topically applied every three hours (five times/day) for two days to New Zealand rabbits in which CNV had been induced by insertion of intrasomal silk sutures (8–0) at 12, 3, 6, and 9 o'clock positions. The amount of DHP penetrating through the epithelium into the cornea was markedly increased by pretreatment with proparacaine before each topical application of the DHP gel.

Control and test rabbits were treated for two days. Post-treatment observation showed that normal corneal tissue eliminated DHP in 48–72 hours after the last gel treatment. Clear portions of the rabbit corneas with CNV did not retain the DHP, but the neovascular portions of the cornea did retain DHP. This same character of elimination and accumulation is expected to occur in human cornea.

Example 3

The photosensitizing gel formulation of example 1 was used topically in the treatment of corneal vascularization of six human patients. An argon green laser (514 nm) was used at an energy level of 204 J/cm$^2$, a spot size of 500 μm which corresponded closely to the size of the vessels encountered, a shot duration of 0.2 seconds, and the number of individual shots varying based on the size and character of the vessel size. After 90 days, the lesions in each of the treated patients got better or cleared.

We claim:

1. A method of photodynamic therapy by a process comprising the steps of:
   locally applying a photosensitizing agent to target tissue consisting essentially of tissues containing blood-carrying vessels supplying an undesired lesion and avoiding adverse general light sensitivity found with intravenous administration of sensitizing agents, the photosensitizing agent being in a pharmaceutically acceptable composition for contact with said target tissue;

illuminating an area consisting essentially of the treated blood-carrying vessels with light from a laser emitting light of a frequency and energy level lower than that used for general tissue irradiation leading to tissue destruction or genetic changes but which excites the photosensitizing agent and coagulates blood in said vessels.

2. A method as in claim 1 wherein the applying step comprises:

topically applying a porphyrin or porphyrin derivative to corneal tissue exhibiting corneal neovascularization.

3. A method as in claim 1 wherein the applying step comprises:

topically applying said photosensitizing agent to neovascular tissue.

4. A method as in claim 1 wherein the applying step comprises:

injecting said photosensitizing agent into said neovascular tissue.

5. A method as in claim 1 wherein the applying step comprises:

topically applying said photosensitizing agent to neoplastic tissue.

6. A method as in claim 1 wherein the applying step comprises:

injecting said photosensitizing agent into said neoplastic tissue.

7. A method as in claim 1 wherein the applying step comprises:

topically applying said photosensitizing agent to cutaneous tissue.

8. A method as in claim 1 wherein the applying step comprises:

topically applying a pharmaceutically acceptable formulation comprising said photosensitizing agent and a bioadhesive polymer.

9. A method as in claim 1 further comprising:

enhancing relative concentration of photosensitizing agent in said lesion by allowing a period of time for healthy tissue adjacent to said lesion to eliminate said photosensitizing agent before illuminating the sensitized lesion area with said laser.

10. A method as in claim 1 wherein the illuminating step comprises:

illuminating said area a plurality of times, each for a duration and in an area sufficient to induce photothrombosis within said blood-carrying vessels.

11. A method for treatment of corneal neovascularization comprising:

topically applying a pharmaceutically acceptable formulation suitable for ophthalmic use comprising a photosensitizing agent and a bioadhesive polymer to an area of a cornea consisting essentially of invading vascular tissue; and illuminating said invading vascular tissue of the cornea with a plurality of laser bursts at a light wavelength which specifically excites the photosensitizing agent and a total laser energy level sufficient to photocoagulate blood in said invading vascular tissue.

12. A formulation for use in photodynamic therapy in an eye, comprising:

a photosensitizer gel comprising a opthalmologically acceptable bioadhesive polymer and a photosensitizing agent which is absorbed by ocular tissue.

13. A formulation according to claim 12 wherein said bioadhesive polymer comprises carboxymethylcellulose.

14. A formulation according to claim 12 wherein said photosensitizing agent is a porphyrin.

15. A formulation according to claim 12 wherein said photosensitizing agent is a phthalocyanine.

16. A formulation according to claim 12 wherein said photosensitizing agent is an indocyanine.

* * * * *